US00PP13957P39

(12) United States Plant Patent
Boeder

(10) Patent No.: US PP13,957 P3
(45) Date of Patent: Jul. 8, 2003

(54) CHRYSANTHEMUM PLANT NAMED 'ENERGY TIME'

(75) Inventor: Mark Roland Boeder, West Wittering (GB)

(73) Assignee: Cleangro Limited (GB)

( * ) Notice: Subject to any disclaimer, the term of this patent is extended or adjusted under 35 U.S.C. 154(b) by 214 days.

(21) Appl. No.: 09/802,056

(22) Filed: Mar. 7, 2001

(65) Prior Publication Data

US 2002/0129418 P1 Sep. 12, 2002

(51) Int. Cl.[7] ..... A01H 5/00

(52) U.S. Cl. ..... Plt./298

(58) Field of Search ..... Plt./298

(56) References Cited

U.S. PATENT DOCUMENTS

PP8,770 P 6/1994 Hesse ..... Plt./77

*Primary Examiner*—Bruce R. Campell
*Assistant Examiner*—Michelle Kizilkaya
(74) *Attorney, Agent, or Firm*—Howrey Simon Arnold & White, LLP

(57) ABSTRACT

A new variety of Chrysanthemum plant named 'Energy Time,' having bright red, spoon shaped ray florets.

1 Drawing Sheet

Latin name of the genus and species: Botanical classification: *Dendranthema grandiflora.*

Variety denomination: The new Chrysanthemum variety denomination is 'Energy Time'.

BACKGROUND OF THE INVENTION

The present invention comprises a new and distinct cultivar of Chrysanthemum botanically known as *Dendranthema grandiflora,* and referred to by the cultivar name 'Energy Time'.

'Energy Time', identified as 21063-0 originated from a cross made by Mark Boeder in a controlled breeding program at Chichester, West Sussex, United Kingdom. The female parent of the new variety is an undistributed, unpatented seedling identified as 90123 and the male parent is an undistributed, unpatented seedling identified as 90421. The new variety 'Energy Time' has been asexually reproduced by vegetative cuttings, at Chichester, West Sussex, United Kingdom and the distinguishing characteristics are retained through successive generations of asexual reproduction.

BRIEF SUMMARY OF THE INVENTION

"Energy Time" is a pot type of Chrysanthemum plant variety having spoon shaped, bright red petals and a single flower type.

COMPARISON WITH PARENT

Plants of the new Chrysanthemum variety 'Energy Time' are similar to the parent cultivar '90123' in plant habitat, flower colour and growth rate. In side-by-side comparisons at Chichester, West Sussex, United Kingdom, under commercial practice, plants of the new Chrysanthemum variety 'Energy Time' differed from plants of the parent cultivar '90421' in the following characteristics.

1. The new variety 'Energy Time' produces spoon shaped petals whereas the parent cultivar '90421' produces flat petals.

2. Plants of the new variety 'Energy Time' have smaller flowers and a shorter inflorescence than plants of the parent cultivar '90421'.

COMPARISON WITH OTHER VARIETIES

Plants of the new Chrysanthemum variety 'Energy Time' are similar to the cultivar 'Rage,' U.S. Plant Pat. No. 8,770, in plant habitat and growth rate. However, in side-by-side comparisons at Chichester, West Sussex, United Kingdom, under commercial practice, plants of the new Chrysanthemum variety 'Energy Time' differed from plants of the cultivar 'Rage' in the following characteristics.

1. The new variety 'Energy Time' produces spoon shaped petals whereas the cultivar 'Rage' produces flat petals.
2. Plants of the new variety 'Energy Time' have a shorter response time than plants of the cultivar 'Rage'.

BRIEF DESCRIPTION OF ILLUSTRATIONS

Typical specimens of the plant and flowers for the new Chrysanthemum variety 'Energy Time' are shown in the accompanying photograph. The colors shown are as true as possible within the usual limits of this kind of illustration.

FIG. 1 is a whole plant view of the new variety 'Energy Time' grown in a pot.

DETAILED BOTANICAL DESCRIPTION

The following description of the new Chrysanthemum variety 'Energy Time' is of plants grown in a greenhouse at Chichester, West Sussex, United Kingdom in the month of December. The cultivar has not been observed under all possible environmental conditions. The phenotype may vary significantly with variations in the environment such as temperature, length of day and light intensity, without any variance in genotype. The commercial classification of the new variety is a pot Chrysanthemum.

Plants of the new variety have been grown successfully under temperature conditions averaging about 19° C. at night and about 17° C. to 22° C. during the day under light conditions of about 5,000 to 6,000 foot candles. The plants respond well to the use of growth retardant, such as two B9 treatments at about 2 gram/liter. To produce a commercial product the plants may be pinched once. The typical container size for commercial growth is 1 liter. It has been observed that the shelf life of the new variety is about 21 days with a response time of about 7.5 weeks.

The new variety may be produced as a spray. The following description is with respect to a plant produced as pot Chrysanthemum. In the description of this new Chrysanthemum variety, color values have been taken from The Royal Horticultural Society Colour Chart (R.H.S.C.C.).

Plant

Plant type: Pot chrysanthemum.
Habit: Upright.
Height: 20–25 cm.
Branching characteristics (describe): Upright spreading.
Length of lateral branches: 10–16 cm.
Number of breaks from pinch: 3–6.
Response time: Near 7.5 weeks.
Vigor: Medium.
Shelf Life: Near 21 days.
Growth retardant type and treatment: 2 applications of 2 gram/liter B9.
Disease susceptibility or resistance observed: No observations.
Propagation:
- *Type.*—Vegetative propagation via stem cuttings.
- *Time to rooting.*—14 days with soil temperatures of 18° C.
- *Rooting habit.*—After 7 Long Days (20 hrs light) first roots emerge from root primordia. After 14 Long Days a complete root system is developed.

Foliage

Number of leaves per lateral branch: 7–12.
Compound or single: Single.
Arrangement of leaves: Alternate.
- *Shape of leaf.*—Typical 5 lobed, oblong.
- *Size of leaf.*—Width (cm): near 3.0–7.0 cm Length (cm): near 5.0–13.5 cm.
- *Leaf apex.*—Mucronate.
- *Base.*—Cordate.
- *Attachment.*—Petioled.
- *Aspect.*—Slight undulating.
- *Margin.*—Palmately lobed.
- *Surface characteristics.*—Top: pubescent. Bottom: pubescent.

Petiole:
- *Color.*—Slightly paler than 139A.
- *Length.*—Near 2.0–4.0 cm.

Venation (describe): Prominent midvein at underside.
- *Color.*—Upper side: near 138B. under side: near 139C.

Color:
- *Mature leaf, upper side.*—Near 139A; under side: Near 147B.
- *Young leaf, upper side.*—Near 137A; under side: near 138A.

Flower

Flower type: Single.
Flower form: Spoon shaped petals.
Number of blossoms per branch: 4–8.
Inflorescence form: Cyme.
- *Depth of fully expanded blossoms.*—Near 2.0–3.0 cm.
- *Diameter of fully expanded blossoms.*—Near 5.0–7.0 cm.

Sepals:
- *Number.*—15–24.
- *Color.*—Near 139A.
- *Length.*—0.4–1.0 cm.
- *Width.*—0.1–0.4 cm.
- *Texture/appearance.*—Pubescent.

Peduncle: length is shortest at the terminal flower and progressively longer moving down the stem; longest length is on average 5.0–8.0, shortest length is on average 3.0–5.0 cm.
- *Length.*—3.0–8.0 cm.
- *Color.*—Near 139B.
- *Surface.*—Pubescent.
- *Habit.*—Slight undulating.
- *Strength.*—Medium.

Pedicel:
- *Length.*—Terminal: 11.5–12.5 cm; lateral 13.0–16.0 cm.
- *Color.*—Near 139B.
- *Surface.*—Pubescent.
- *Habit.*—Slight undulating.
- *Strength.*—Medium.

Ray florets:
- *Form/shape.*—Spoon shape.
- *Texture/appearance.*—Matte.
- *Number per flower.*—25–39.
- *Length.*—1.0–3.5 cm Width: 0.2–0.9 cm.
- *Apex.*—Rounded.
- *Base.*—Tubular.
- *Margin.*—Entire.

Disc florets:
- *Form/shape.*—Tubular.
- *Texture/appearance.*—Cylindrical.
- *Number per flower.*—180–220.
- *Length.*—0.6–0.8 cm; Width near 0.1 cm.
- *Diameter of disc.*—0.8–1.2 cm.

Fragrance: Very faint.
Flower bud (at onset of color):
- *Length.*—0.8–1.0 cm.
- *Diameter.*—0.9–1.1 cm.
- *Form/shape.*—Spherical.

General flower color:
1. *Ray florets, upper side.*—Immature: Near 46A. Mature: Near 46A. Older/fading: Near 46B.
2. *Ray florets, under side.*—Immature: Near 37A. Mature: Near 37A. Older/fading: Near 37B.
3. *Disc florets.*—Immature: Near 138B. Mature: Near 12A. Older/fading: Near 12C.

Flower progression with age: Flower form of ray florets start as almost completely tubular at the moment of the opening of the flower. Later the tips of the ray florets become flat in a cross section. Slightly fading flower color.

Reproductive Organs

Ray florets: Pistillate.
- *Pistil number.*—About 5.
- *Stigma color.*—Near 13B.
- *Stigma shape.*—Fork.
- *Style color.*—Near 13D.
- *Style length.*—0.3–0.6 cm.

Disc florets: Pistillate.
- *Pistil number.*—About 5.
- *Stigma color.*—Near 13B.

*Stigma shape.*—Fork.
*Style color.*—Near 13D.
*Style length.*—0.1–0.4 cm.
Staminate:
*Stamen number.*—About 5.
*Anther shape.*—Thread.
*Anther color.*—Near 13B.
*Pollen color.*—Near 14A.
*Pollen quantity.*—Abundant.

What is claimed is:

1. A new and distinct variety of Chrysanthemum plant, substantially as described and illustrated herein.

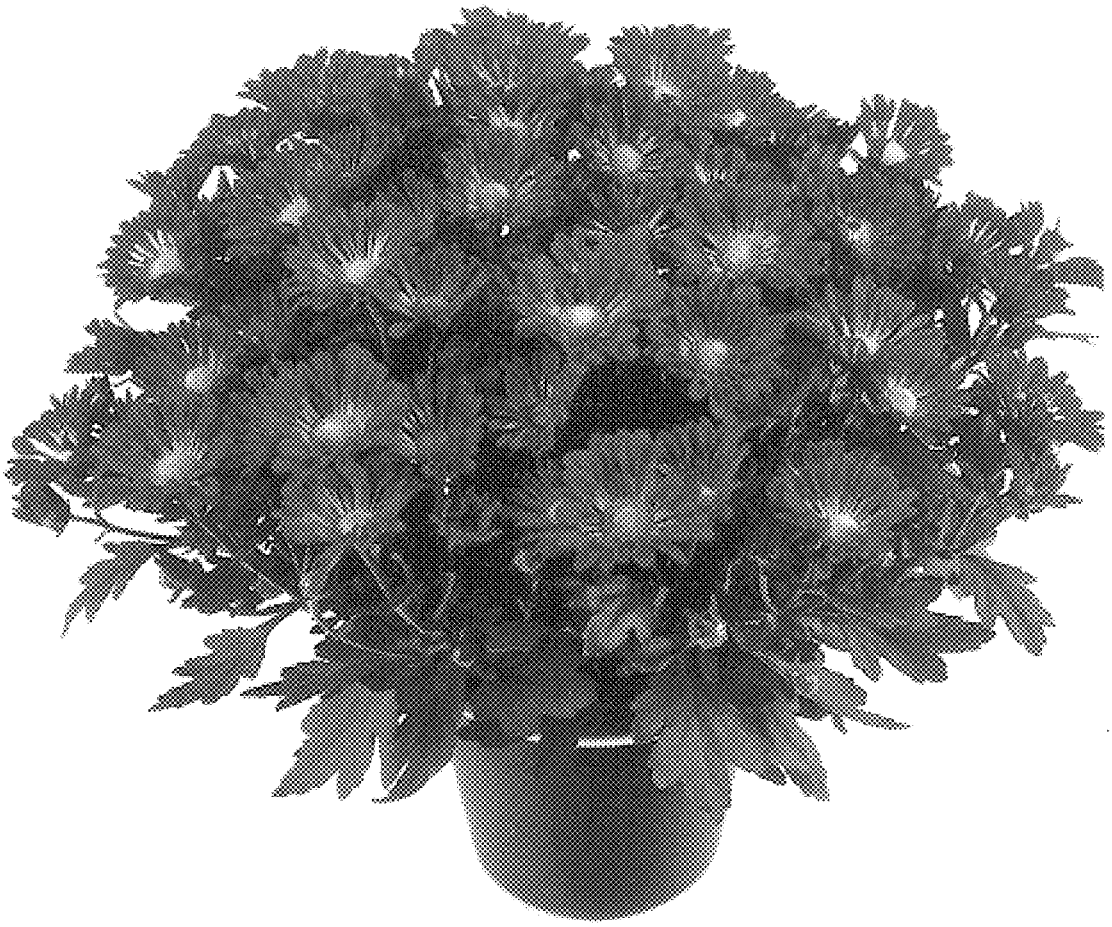

* * * * *